(12) United States Patent
Boynton et al.

(10) Patent No.: US 6,429,649 B1
(45) Date of Patent: Aug. 6, 2002

(54) EDDY CURRENT TESTING PROBE

(75) Inventors: Jayne L. Boynton, Jeannette; Gary Peter Pierini, Pittsburgh, both of PA (US)

(73) Assignee: Westinghouse Electric Company LLC, Pittsburgh, PA (US)

( * ) Notice: Subject to any disclaimer, the term of this patent is extended or adjusted under 35 U.S.C. 154(b) by 47 days.

(21) Appl. No.: 09/609,788

(22) Filed: Jul. 3, 2000

Related U.S. Application Data

(60) Provisional application No. 60/143,726, filed on Jul. 14, 1999.

(51) Int. Cl.[7] .......................... G01N 27/72; G01N 27/82
(52) U.S. Cl. ........................................ 324/220; 439/102
(58) Field of Search .............................. 324/220, 262, 324/226, 227, 219, 207.18, 238; 439/102, 537

(56) References Cited

U.S. PATENT DOCUMENTS

| | | | |
|---|---|---|---|
| 4,438,399 A | * | 3/1984 | Schnabl et al. ............. 324/220 |
| 4,851,773 A | * | 7/1989 | Rothstein ................... 324/220 |
| 4,856,337 A | | 8/1989 | Metala et al. |
| 5,279,168 A | | 1/1994 | Timm |

* cited by examiner

*Primary Examiner*—Edward Lefkowitz
*Assistant Examiner*—Subhash Zaveri

(57) ABSTRACT

A replaceable eddy current probe for inspecting small (¾ inch diameter or smaller) tubes of heat exchangers has a head portion with bobbin coils and a delivery conduit connector portion with a flexible conduit having a first end extending from the head portion and a second end extending to the connector portion. The connector portion has electrical terminal connections electrically connected to the bobbin coils by wires extending through the flexible conduit. The connector portion also has a housing with a surface surrounding the electrical terminal connections and the surface has a 360° delivery conduit mechanical interlock which may be a recess or a proturburance for mating with a proturberance or recess of a delivery conduit. The 360° interlock provides a robust connection which will not separate during high speed pushing and pulling forces and twisting through tight turns of U-bends.

2 Claims, 1 Drawing Sheet

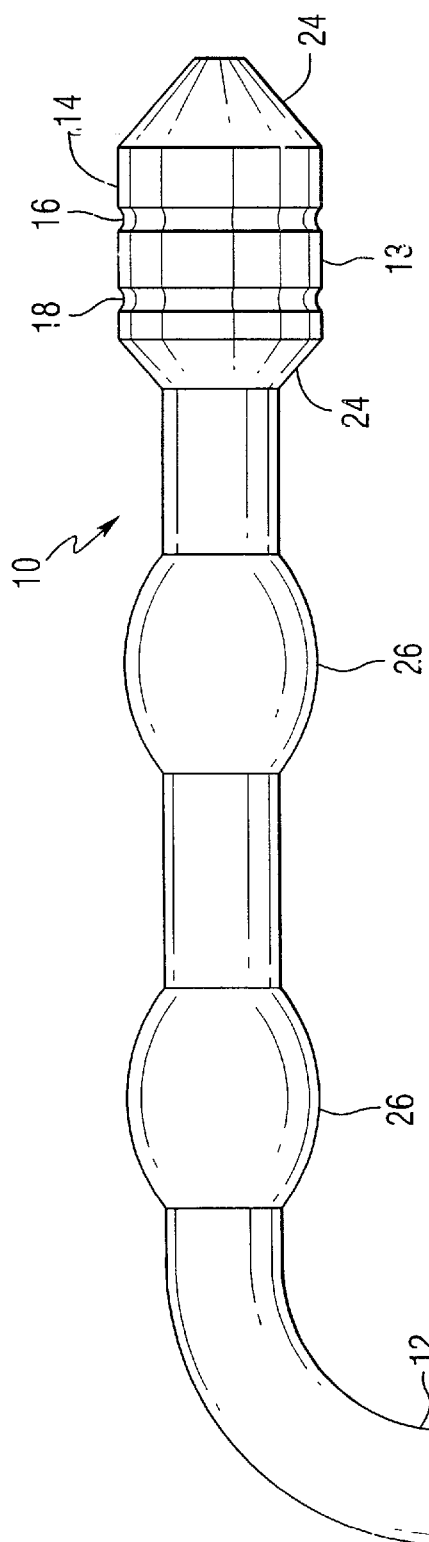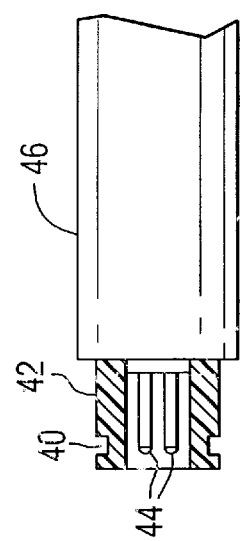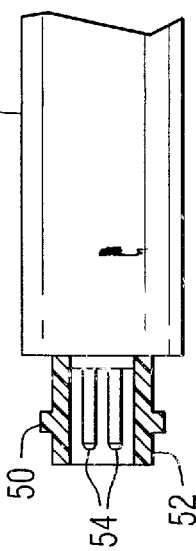

EDDY CURRENT TESTING PROBE

CROSS REFERENCE

This application claims the benefit of the filing date of Provisional Patent Application No. 60/143,726, filed Jul. 14, 1999.

BACKGROUND OF THE INVENTION

The invention relates to eddy current probes for inspecting long tubular members and more particularly to bobbin probes that are attached to the ends of flexible conduits for inspecting tubes at high speeds.

Eddy current probes are employed to inspect small (about three quarter of an inch or smaller) tubes of tube bundles of shell and tube heat exchangers having hundreds or even thousands of tubes and the like. In a commercial application of particular concern to the inventors, the tube bundles are U-tubes extending from a tube sheet of steam generators of the type manufactured by the assignee of the present invention for use in commercial nuclear power plants for generating electricity. The U-tubes of such heat exchangers may extend for thirty feet or more from their tube sheets. To inspect the tubes of such steam generators, an elongated probe attached to the end of a long section of flexible delivery conduit is robotically introduced into a tube, moved through the tube at relatively high speeds to inspect the straight and bend portions, withdrawn from the tube and then introduced into another tube in the tube bundle. Bobbin probes are frequently employed because these probes can provide accurate indications of cracking, corrosion and other flaws. These inspections are generally conducted on critical path schedules so that they must be accurately conducted at high speeds. U.S. Pat. No. 5,279,168 discloses a bobbin probe assembly that may be employed to inspect U-tubes of steam generators. Other eddy current probe assemblies are disclosed in the following U.S. Pat. Nos.: 4,438,399; 4,889,679; 4,668,912; 4,683,361; 4,856,337; 5,105,876; 5,134,367; 5,247,251. These patents, including U.S. Pat. No. 5,279,168, are hereby incorporated for their disclosures of the structures and uses of eddy current probes for testing tubing.

The majority of failures of bobbin probes used commercially are in the heads of the probes rather than in their flexible delivery conduits. Thus, the art has developed replaceable heads in order to eliminate the cost of having to replace the entire probe and delivery conduit and to reduce the probe change out time. As is shown by the U.S. Pat. No. 4,438,399, these heads may have bayonet coupling designs (or "J" locks) for readily changing probes. However, these couplings may detach when subjected to high speed pulling and pushing forces and twisting in the tight inner rows of the inner tubes of the U-tube bundles.

SUMMARY OF THE INVENTION

It is an object of the present invention to provide a bobbin probe head having a more rugged quick release coupling. It is a further object to provide a bobbin probe head that will not detach from a flexible delivery conduit during high speed pulling and pushing in the tight inner bends of U-tubes.

With these objects in view, the present invention resides in an eddy current testing probe for releasably coupling with a delivery conduit. The probe has a head portion with bobbin coils and a delivery conduit connector portion, with a flexible conduit having a first end extending from the head portion to a second end extending to the connector portion. The connector portion has electrical terminal connections electrically connected to the bobbin coils by wires extending through the flexible conduit and has a housing with a surface surrounding the electrical terminal connections. Importantly, the housing surface surrounding the electrical terminal connections has a 360° delivery conduit mechanical interlock. The interlock may in one embodiment of the present invention be a recess for receiving a proturburance on the delivery conduit or may in a second embodiment be a proturburance for engaging a recess in the delivery conduit. Advantageously, a interlock provides a circumferential mechanical lock which will not readily disengage when a probe and its delivery conduit move and twist at high speeds through small tubes and around tight bends of U-tubes.

BRIEF DESCRIPTION OF THE DRAWINGS

The invention as set forth in the claims will become more apparent from the following detailed description of a preferred embodiment thereof shown, by way of example only, in the accompanying drawings, wherein:

FIG. 1 is a partially cut-a-way representation of a bobbin probe of the present invention.

FIG. 2 is a partially cut-a-way representation of a flexible conduit that may be employed to deliver the bobbin probe of FIG. 1 in a tube.

FIG. 3 is a partially cut-a-way representation of another flexible conduit that may be employed to deliver the bobbin probe of FIG. 1 in a tube.

DESCRIPTION OF THE PREFERRED EMBODIMENT

Referring now to the drawing in detail, there is shown a bobbin probe 10 of the present invention. The probe 10 includes a flexible conduit 12 with a head portion 13 including a bobbin assembly 14 at one end. The bobbin assembly 14 has coils 16 and 18 that are connected by wires 19 to electrical terminal connections 20 of a delivery conduit connector portion 22 extending from the other end of the flexible conduit 12. The head portion 13 also has centering pedals 24 at either end for centering the assembly 14 in a tube (not shown). The flexible conduit 12 also has centering beads 26 along its length for centering the flexible conduit 12 in a tube (not shown).

The delivery conduit connector portion 22 also has a housing member 28 with a surface 29 surrounding the electrical terminal connections 20 with flexible protuberances 30 and recesses 32 extending around the electrical terminal connections 20 of the connector 22. The protuberances 30 of the connector 22 may be dimensioned and located on the housing member 28 to engage a mating recess 40 of a member 42 surrounding the electrical connections 44 of a flexible delivery conduit 46 shown in FIG. 2. In another embodiment of the present invention, the recesses 32 of the connector 22 may be dimensioned and located on the member 28 to engage a mating protuberance 50 of a member 52 surrounding the electrical connections 54 of a flexible delivery conduit 56 shown in FIG. 3. The proturburances 30 and the recesses 32 extend 360° around the surface 29. Also, there is at least one proturburance 30 and/or recess 32 axially disposed between the flexible conduit 12 and the distal end 38 of the electrical terminal connections 20. In other embodiments the surface 29 may have either protuberances 30 or recesses 32. Also, the protuberances 30 and/or recesses 32 may be on an internal surface 29 of the housing member 28 (as shown) or on an external surface (not shown).

The flexible delivery conduits 46 and 56 are the means by which a robot arm and probe pusher (not shown) can introduce the bobbin probe head 10 into a tube and then push and pull the bobbin probe head 10 at high speeds through the straight lengths and bends of tubes of a commercial nuclear steam generator (not shown) and the like. See, e.g., U.S. Pat. Nos. 4,856,337; 5,105,876 and 5,279,168 for a discussion of eddy current inspections of steam generator tubes using eddy current probe devices and related equipment.

While a present preferred embodiment of the present invention has been shown and described, it is to be understood that the invention may be otherwise variously embodied within the scope of the following claims of invention.

What is claimed is:

1. An eddy current testing probe for releasably coupling with a delivery conduit, the probe comprising: a head portion with bobbin coils and a delivery conduit connector portion, a flexible conduit having a first end extending from the head portion and a second end extending to the connector portion, the connector portion having electrical terminal connections electrically connected to the bobbin coils by wires extending through the flexible conduit, the connector portion also having a housing with a surface surrounding the electrical terminal connections, the surface having a 360° delivery conduit mechanical interlock, wherein the mechanical interlock is a 360° flexible proturberance in the surface surrounding the electrical terminal connections adapted to mechanically engage a recess of a delivery conduit.

2. The probe of claim 1, wherein the electrical terminal connections have a distal end and the proturberance is disposed between the flexible conduit the distal end of the electrical terminal connections.

* * * * *